(12) United States Patent
Lee et al.

(10) Patent No.: US 9,713,547 B2
(45) Date of Patent: Jul. 25, 2017

(54) MALE INCONTINENCE FLUID CAPTURING DEVICE AND METHODS

(71) Applicant: IDLE HANDS SOLUTIONS, INC., Laguna Niguel, CA (US)

(72) Inventors: Eric S. Lee, Laguna Niguel, CA (US); Daniel Kincade, Encinitas, CA (US)

(73) Assignee: Idle Hands Solutions Inc., Laguel, CA (US)

(*) Notice: Subject to any disclaimer, the term of this patent is extended or adjusted under 35 U.S.C. 154(b) by 81 days.

(21) Appl. No.: 14/456,936

(22) Filed: Aug. 11, 2014

(65) Prior Publication Data

US 2015/0045757 A1 Feb. 12, 2015

Related U.S. Application Data (60) Provisional application No. 61/865,108, filed on Aug. 12, 2013.

(51) Int. Cl.
*A61F 5/44* (2006.01)
*A61F 5/453* (2006.01)
*A61F 13/471* (2006.01)
*A61F 5/48* (2006.01)

(52) U.S. Cl.
CPC .......... *A61F 5/4401* (2013.01); *A61F 5/4408* (2013.01); *A61F 5/453* (2013.01); *A61F 5/48* (2013.01); *A61F 13/471* (2013.01); *A61F 2005/4402* (2013.01)

(58) Field of Classification Search
CPC ...... A61F 13/471; A61F 5/4401; A61F 5/453; A61F 6/02; A61F 2006/044
See application file for complete search history.

(56) References Cited

U.S. PATENT DOCUMENTS

| | | | | |
|---|---|---|---|---|
| 3,863,638 A | * | 2/1975 | Rogers, III | A61F 5/453 604/352 |
| 4,064,880 A | * | 12/1977 | Logan | A61F 5/4401 128/856 |
| 4,601,716 A | * | 7/1986 | Smith | A61F 5/4401 604/349 |
| 4,668,229 A | | 5/1987 | Fago et al. | |
| 4,863,448 A | | 9/1989 | Berg | |
| 5,366,449 A | | 11/1994 | Gilberg | |

(Continued)

FOREIGN PATENT DOCUMENTS

| | | | | |
|---|---|---|---|---|
| CH | 695660 A5 | * | 7/2006 | A61F 5/453 |
| DE | 202012003646 | * | 5/2012 | A61F 5/453 |
| WO | WO 8402070 A1 | * | 6/1984 | A61F 5/4401 |

*Primary Examiner* — Kathryn E Ditmer
(74) *Attorney, Agent, or Firm* — Mark David Torche; Patwrite LLC (57) ABSTRACT

A fluid capturing device is described herein that can contain and manage urine or other secretions that may be emitted from a penis. The fluid capturing device can include a sheath that conforms to at least part of the penis. For example, the sheath can include a proximal portion that covers at least a part of the shaft of the penis and a distal portion that covers at least a part of the head of the penis. In addition, the fluid capturing device can include an absorbent that can absorb the excretions or emissions from the penis. The absorbent can be removed and replaced from the sheath, including while the sheath is at least partially secured to the penis.

19 Claims, 8 Drawing Sheets

(56) References Cited

U.S. PATENT DOCUMENTS

| | | | |
|---|---|---|---|
| 5,513,654 A * | 5/1996 | Delson | A61F 6/04 128/844 |
| 5,531,725 A * | 7/1996 | Steer | A61F 5/453 128/844 |
| 5,643,235 A | 7/1997 | Figuerido | |
| 5,695,485 A | 12/1997 | Duperret et al. | |
| 5,702,381 A | 12/1997 | Cottenden | |
| 5,855,206 A * | 1/1999 | Ireland | A61F 6/04 128/842 |
| 6,105,174 A | 8/2000 | Nygren et al. | |
| 6,113,582 A | 9/2000 | Dwork | |
| 6,209,142 B1 | 4/2001 | Mattsson | |
| 6,336,919 B1 | 1/2002 | Davis et al. | |
| 6,416,500 B1 | 7/2002 | Wada et al. | |
| 6,479,726 B1 | 11/2002 | Cole | |
| 6,949,090 B1 * | 9/2005 | Leers | A61F 13/471 604/386 |
| D613,855 S | 4/2010 | Pena | |
| 8,250,677 B2 | 8/2012 | Nicolosi et al. | |
| 8,696,641 B1 | 4/2014 | Williams, III | |
| 2004/0006321 A1 * | 1/2004 | Cheng | A61F 5/453 604/349 |
| 2006/0229576 A1 | 10/2006 | Conway et al. | |
| 2008/0011310 A1 * | 1/2008 | Anderson | A61F 2/0054 128/885 |
| 2008/0234642 A1 * | 9/2008 | Patterson | A61F 5/441 604/319 |
| 2010/0125260 A1 * | 5/2010 | White | A61F 13/471 604/356 |
| 2011/0054428 A1 | 3/2011 | Hill | |
| 2012/0222688 A1 | 9/2012 | Farner et al. | |
| 2013/0030401 A1 * | 1/2013 | Heyman | A61F 13/471 604/385.03 |

* cited by examiner

MALE INCONTINENCE FLUID CAPTURING DEVICE AND METHODS

CROSS-REFERENCE TO RELATED APPLICATION

The current application claims priority under 35 U.S.C. §119(e) to U.S. Provisional Patent Application Ser. No. 61/865,108, filed on Aug. 12, 2013 and entitled "LP Shield (Leak Protector)," which is incorporated by reference herein in its entirety.

TECHNICAL FIELD

The subject matter described herein relates to fluid capturing devices and associated methods.

BACKGROUND

A wide variety of medical conditions may contribute to a male experiencing uncontrolled or unintentional leakage of fluids from the penis. These causes may be acute or may be chronic in duration. Typical causes can include, infections of the genital or urinary tract, side effects from medications, physiological responses to medical procedures, medical procedures involving the penis, aging, disease of genital or urinary glands or organs or recent sexual activity.

Some products specifically deal with urinary incontinence, from indwelling devices (e.g., catheters) to gross absorbents (e.g., diapers and pads), and these products can have some drawbacks. For example, these products can be uncomfortable and can generate noises during routine activities that can lead to loss of privacy or embarrassment. Further, those who use these product may need to carry a supply of large bulky replacements because at least some of these products must be changed (e.g., to avoid the potential for leakage, odor, etc.).

SUMMARY

Aspects of the current subject matter can include devices and methods for capturing fluid from a penis. Additional application can also be used for the disclosed device, some of which are discussed herein.

In one aspect, a fluid capturing device for positioning over at least a part of a penis is described, which can include a sheath including a proximal portion that is tubular for extending around at least a part of a shaft of a penis and a distal portion that is contoured to cover at least a part of a head of the penis, the proximal portion can include a first opening having a first diameter and the distal portion can include a second opening having a second diameter. In addition, the fluid capturing device can include an absorbent positioned along an inner surface of the sheath and the absorbent can be configured to be removable through the second opening.

In some variations one or more of the following features can optionally be included in any feasible combination. For example, the fluid capturing device can include a sheath having a retention feature that assists in securing the position of the sheath relative to the penis. In addition, in some embodiments the retention feature can include a rolled cuff positioned at a proximal end of the sheath. Additionally, some embodiments of the retention feature can include an external flap that is configured to form a secured position and an unsecured position. Furthermore, some embodiments of the retention feature can include either a compressive sleeve positioned at a proximal end of the sheath or a retaining ring that is configured to provide a circumferential compressive force around a part of the sheath. In addition, some embodiments of the retention feature can include an adjustable retaining cord that extends through a circumferential pocket at a proximal end of the sheath. Additionally, some embodiments of the retention feature can include a deformable elastic element extending through a circumferential pocket at a proximal end of the sheath.

In addition, the fluid capturing device can further include a grasping feature that is at least one of coupled to or integrated with the absorbent, wherein the grasping feature is configured to assist with at least removing the absorbent from the sheath. Additionally, some embodiments of the fluid capturing device can have the absorbent made out of at least one of a directionally permeable material, an absorbent material, and a moisture resistant material. In some embodiments, the absorbent can include at least one external positioning feature for assisting with securing the positioning of the absorbent relative to the sheath. For example, the external positioning feature can include one or more of an adhesive and an extruded geometric feature.

Additionally, some embodiments of the absorbent can include a reusable component and a disposable component. Furthermore, the absorbent can form a collapsed configuration and an expanded configuration. At least some embodiments of the absorbent can include a hollow shape having a cavity that covers at least a part of a head of the penis.

An example method of the fluid capturing device can include inserting a part of a penis into a fluid capturing device, the fluid capturing device having a sheath including a proximal portion that is tubular for extending around at least a part of a shaft of the penis and a distal portion that is contoured to cover at least a part of a head of the penis. In addition, the fluid capturing device can have the proximal portion including a first opening having a first diameter and the distal portion including a second opening having a second diameter, and the fluid capturing device can further include an absorbent positioned along an inner surface of the sheath with the absorbent configured to be removable through the second opening.

In some variations of the method, the method can include removing the absorbent from the fluid capturing device while the sheath is secured to the penis. In addition, some methods of the fluid capturing device can include that wherein the absorbent is removed from the sheath through the second opening. Additionally, some methods of the fluid capturing device can include inserting a new absorbent into the sheath through a slit along a side of the sheath, wherein the new absorbent is inserted while the sheath is secured to the penis. Furthermore, some methods of the fluid capturing device can include securing the sheath to the penis with a retention feature.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

The present disclosure describes various embodiments of a fluid capturing device that is designed to contain and manage urine or other secretions that may be emitted from the urethra of a penis (discharges). The fluid capturing device can also contain and manage secretions from other sources on the structure of the penis as well. For example, the fluid capturing device can provide a user with a sanitary and discrete method for managing discharges without the user having to alter the user's attire, physical activities or compromise privacy. The fluid capturing device described herein can provide protection against discharge or leakage in a manner that is as minimally intrusive.

The fluid capturing device can provide containment means to gather and control any of a multitude of excretions or emissions that can be secreted from the penis. In addition, the fluid capturing device can be designed to be anatomically accommodating to the penis, minimally intrusive to the user and be completely independent of the user's choice of undergarments.

The fluid capturing device can include a sheath that conforms to at least part of the penis, and can include a proximal portion that covers at least a part of the shaft of the penis and a distal portion that covers at least a part of the head of the penis. The sheath can be configured to conform to a shape and contour of at least a flaccid penis. In addition, the fluid capturing device can include an absorbent that can absorb the excretions or emissions from the penis. The absorbent can be removed and replaced from the sheath, including while the sheath is at least partially secured to the penis. For example, a used absorbent can be removed from the sheath in order to be replaced with a new absorbent, such as in order to prevent over-absorption of fluids in the absorbent and prevent leakage, sanitation reasons, etc.

In addition, the fluid capturing device can include a first opening in the proximal portion of the sheath and a second opening in the distal portion of the sheath. The first opening can be sized and shaped to allow the penis to be inserted and positioned within the sheath. The second opening can be sized and shaped to allow the absorbent to be removed from the sheath, while also preventing the absorbent from unwanted removal from the sheath. The absorbent can include a variety of materials that can assist with absorbing a variety of fluids (e.g., excretions, emissions). In addition, the absorbent can include features that can assist with securing the position of the absorbent in the sheath.

Additionally, a grasping feature can be incorporated with or coupled to the absorbent, which can assist a user with removing (e.g., via pulling) the absorbent from the sheath, including while the user is wearing the sheath. For example, while wearing the fluid capturing device, the user can pull on the grasping feature and remove the absorbent through the second opening. While still wearing the sheath, the user can replace the absorbent with a new absorbent, such as through a slit along the length of the sheath. The slit can also provide a way to remove the penis from the sheath, such as during urination, without completely detaching the fluid capturing device from the penis. This can also allow for discrete use of the fluid capturing device. The fluid capturing device can also include one or more retaining features that can assist with securing the position of the fluid capturing device relative to the penis.

Figure 1:
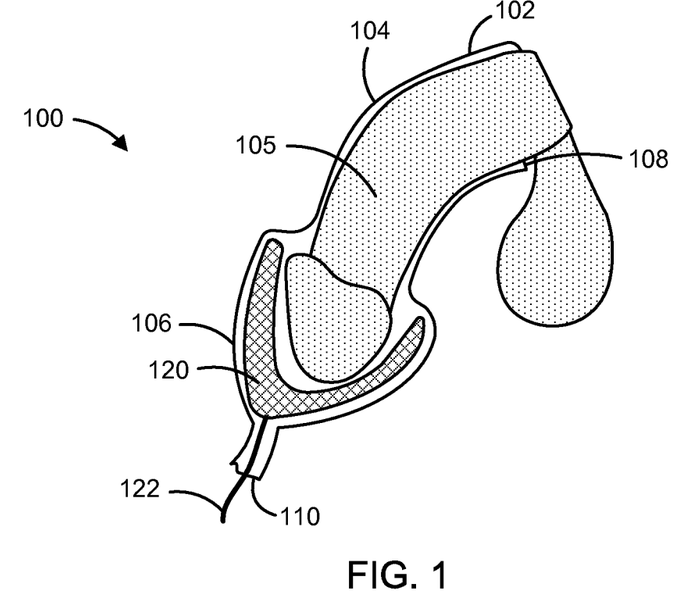
FIG. 1 shows a cross-section view of one embodiment of a fluid capturing device positioned over a penis, with the fluid capturing device including a sheath and removable absorbent.

FIG. 1 illustrates an embodiment of a fluid capturing device 100 that can be removably positioned over at least a part of a penis 105 for collecting fluids. The fluid capturing device 100 can include a sheath 102 including a proximal portion 104 and a distal portion 106. The proximal portion 102 can include a tubular structure that can extend along a part of a shaft of the penis 105. The distal portion 106 can be sized and shaped to conform to at least a part of a head of the penis. In addition, the proximal portion 102 can include a first opening 108 having a first diameter at a proximal end of the proximal portion 102 and the distal portion 106 can include a second opening 110 having a second diameter, which can be smaller than the first diameter. The first opening 108 can be sized and shaped to allow insertion and positioning of the penis within the fluid capturing device 100. The second opening 110, which can, for example, be positioned at a distal end of the distal portion 106, can allow for removal of an absorbent, as will be discussed in greater detail below. Although shown and described as having the second opening 110 for removal of the absorbent positioned at the distal end of the distal portion 106, the second opening 110 can be positioned anywhere along the distal portion 106, and can additionally or alternatively be positioned along the proximal portion 104.

In addition, the fluid capturing device 100 can include an absorbent 120 that can be positioned in the distal portion 106 of the sheath 102. The absorbent 120 can at least partially cover or surround the head of the penis 105, which can allow for capturing of fluid excreted, for example, through the urethra. However, although the absorbent 120 is shown as being positioned in the distal portion 106 of the sheath 102 and surrounding the head of the penis, the absorbent 120 can be positioned anywhere in the sheath 102 and have any number of shapes and sizes, such as in order to accommodate other uses of the device (e.g., providing sanitary covering over a wound on the penis, applying medication to one or more parts of the penis, etc.).

The absorbent 120 can be attached to or integrated with a grasping feature 122, which can assist with either removing or replacing the absorbent 120. For example, a user can pull on the grasping feature 122 in order to pull the absorbent 120 out through the second opening 110. In addition, a user an insert a new absorbent 120 through either the first opening 108 or through a slit in the sheath (see, for example, FIGS. 22A-22D) and use the grasping feature 122 to assist with positioning the absorbent 120 within the sheath 102. The absorbent 120 can be either removed from the sheath 102 or inserted into the sheath 102 for use while the user is wearing the fluid capturing device 100.

Figure 2:
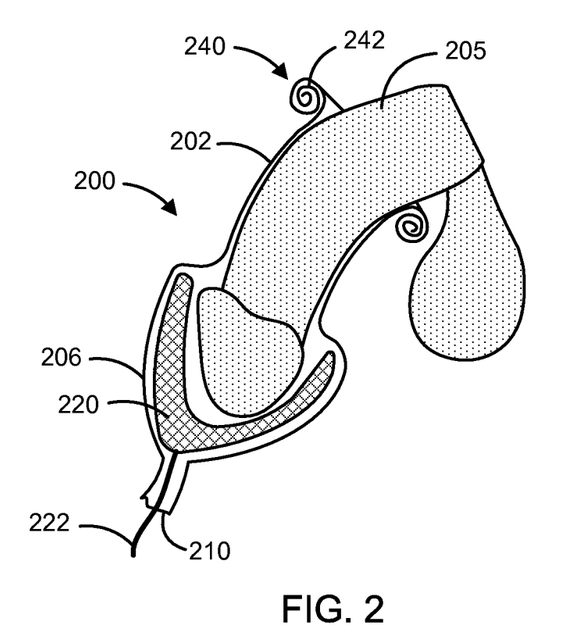
FIG. 2 shows a cross-section view of another embodiment of a fluid capturing device positioned over a penis, with the fluid capturing device having a retention feature including a rolled cuff.

FIG. 2 illustrates another embodiment of a fluid capturing device 200 that can be removably positioned over at least a part of a penis 205 for collecting fluids. The fluid capturing device 200 can include a sheath 202 and a removable absorbent 220, which can be replaced with a new absorbent 220. For example, the absorbent 220 can be removed from the sheath through a second opening 210 of the sheath, including while the sheath is positioned on the penis 205, such as described above. Additionally, the sheath 202 can have a retention feature 240 that can assist with securing the position of the fluid capturing device 200 relative to the penis 205.

As shown in FIG. 2, the retention feature can include a rolled cuff 242. The rolled cuff 242 can be made out of extra material at the proximal end of the sheath 202. The extra material can be used to roll up in order to create a circumferential compressive force along a part of a shaft of the penis 205. The extra material used to form the rolled cuff 242 can be made out of the same or different material than the rest of the sheath 202.

Figure 3A:
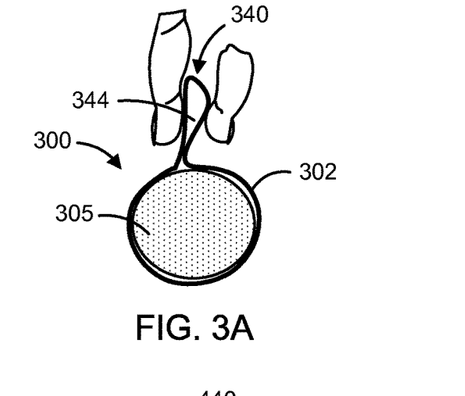
FIG. 3A shows a top view of yet another embodiment of a fluid capturing device positioned over a penis, with the fluid capturing device having a retention feature including an external flap in an unsecured position.
Figure 3B:
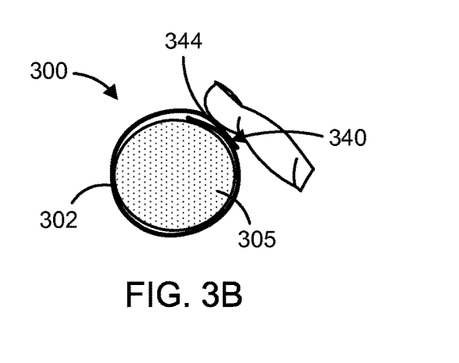
FIG. 3B shows a top view of the fluid capturing device of FIG. 3A with the external flap in a secured position.

FIGS. 3A and 3B illustrate another embodiment of a fluid capturing device 300 that can be removably positioned over at least a part of a penis 305 for collecting fluids. For example, the device 300 can include a sheath 302 and removable absorbent that can be replaced with a new absorbent, as described above. For example, the absorbent can be removed from the sheath 302 through a second opening of the sheath 302, including while the sheath 302 is positioned on the penis 205, such as described above. Additionally, the sheath 302 can have a retention feature 340 that can assist with securing the position of the device 300 relative to the penis 305.

The retention feature 340 can include an external flap 344 that can form a secured position (see FIG. 3B) and an unsecured position (see FIG. 3A). The external flap 344 can be made out of extra material from the proximal portion of the sheath 320 (e.g., adjacent the proximal end of the sheath) that can be folded to form the external flap 344. Alternatively, the external flap 344 can be a feature that is coupled to a side of the sheath 302 and can assist with constricting the sheath around the penis for securing the positioning of the sheath 302 relative to the penis 305. The external flap 344 can include an adhesive that can assist with securing the external flap 344 in the secured position. The adhesive can also allow the external flap to become unsecured from the secured position, such as in order to remove the device 300 from the penis 305.

Figure 4:
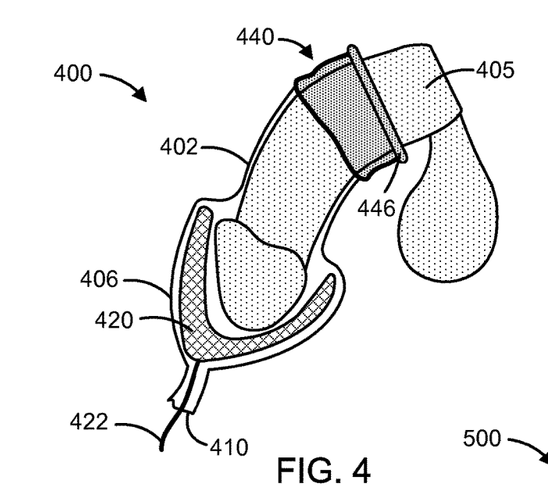
FIG. 4 shows a side view of another embodiment of a fluid capturing device positioned over a penis, with the fluid capturing device having a retention feature including a compressive sleeve.

FIG. 4 illustrates another embodiment of a fluid capturing device 400 that can be removably positioned over at least a part of a penis 405 for collecting fluids. For example, the device 400 can include a sheath 402 and removable absorbent 420 that can be replaced with a new absorbent, as described above. For example, the absorbent 420 can be removed from the sheath through a second opening 410 of the sheath 402, including while the sheath is positioned on the penis 405, such as described above. Additionally, the sheath 402 can have a retention feature 440 that can assist with securing the position of the device 400 relative to the penis 405.

The retention feature 440 can include an elastic compressive sleeve 446 that can provide a circumferential compressive force around the shaft of the penis 405. The compressive sleeve 446 can be made out of a material that can apply the circumferential compressive force. For example during use, the compressive sleeve 446 can be expanded in order to allow the penis to be inserted and positioned within the sheath 402. The compressive sleeve 446 can be relaxed in order to allow the compressive sleeve 446 to apply the circumferential compressive force and assist with securing the sheath 402 to the penis 405.

The compressive sleeve 446 can be made out of the same or different material than the remaining part of the sheath 402. In addition, the compressive sleeve 446 can be attached to the sheath 402 in a variety of ways, including bonded, sewn, etc. The compressive sleeve 446 can include surface features along an inner surface of the compressive sleeve 446 that can assist with securing the position of the compressive sleeve 446 relative to the shaft of the penis (e.g. via friction). Additionally, the compressive sleeve 446 can include features that encourage ventilation (e.g., porous material) between the skin of the penis and the compressive sleeve 446.

Figure 5A:
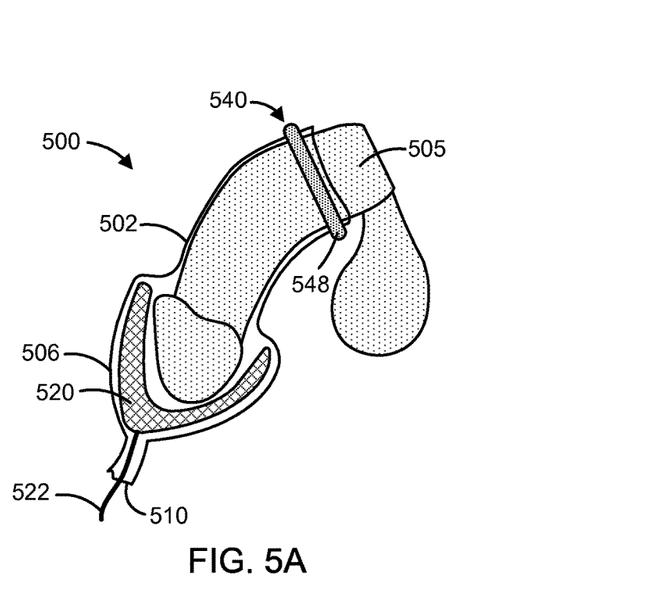
FIG. 5A shows a side view of another embodiment of a fluid capturing device positioned over a penis, with the fluid capturing device having a retention feature including a retaining ring.
Figure 5B:
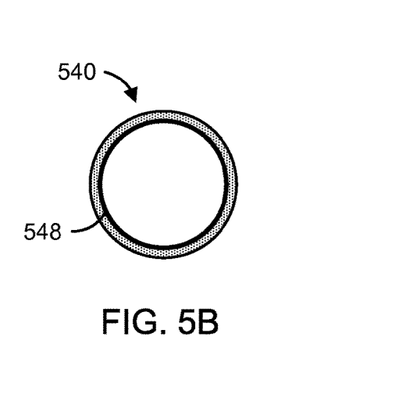
FIG. 5B shows a top view of the retaining ring of FIG. 5A.

FIGS. 5A and 5B illustrate another embodiment of a fluid capturing device 500 that can be removably positioned over at least a part of a penis 505 for collecting fluids. For example, the device 500 can include a sheath 502 and removable absorbent 520 that can be replaced with a new absorbent 520, as described above. For example, the absorbent 520 can be removed from the sheath 502 through a second opening 510 of the sheath 502, including while the sheath 502 is positioned on the penis 505, such as described above. Additionally, the sheath 502 can have a retention feature 540 that can assist with securing the position of the device 500 relative to the penis 505.

The retention feature 540 can include a retaining ring 548, which can be releasably coupled to the sheath 502. The retaining ring 548 can be a separate part from the sheath 502 such that it can be coupled and completely removed from the sheath 502, as shown in FIG. 5B. The retaining ring 548 can apply a circumferential compressive force around the sheath 502, which can assist with securing the position of the sheath 502 relative to the penis 505. The retaining ring 548 can have a ring shape with a circular or rounded (e.g., elliptical, etc.) profile. In addition, the retaining ring 548 can be made out of one or more of a variety of materials, including elastomeric materials, such as silicone, latex rubber, synthetic rubber, etc. Additionally, the retaining ring 548 can be made in a variety of sizes in order to achieve a desired level of retention of the sheath 502 and comfort for the user.

For example, during use, the retaining ring 548 can be expanded in order to allow the retaining ring 548 to be positioned over the sheath 502 and shaft of the penis 505. The retaining ring 548 can be allowed to relax over the sheath 502 that has been positioned over the penis 505 in order to allow the retaining ring 548 to retain the sheath 502 in the desired position over the penis 505.

Figure 6A:
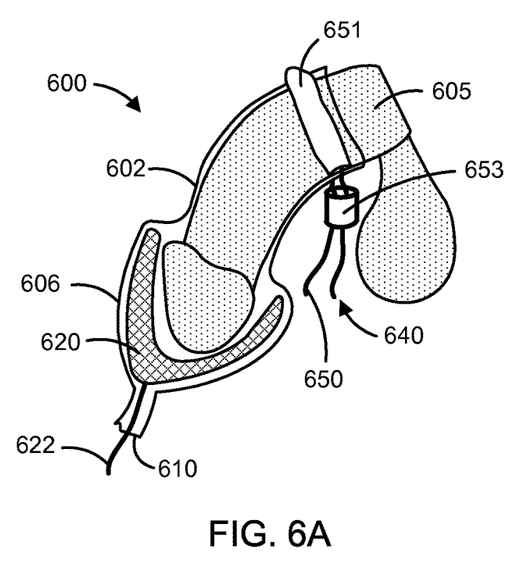
FIG. 6A shows a side view of another embodiment of a fluid capturing device positioned over a penis, with the fluid capturing device having a retention feature including a retaining cord.
Figure 6B:
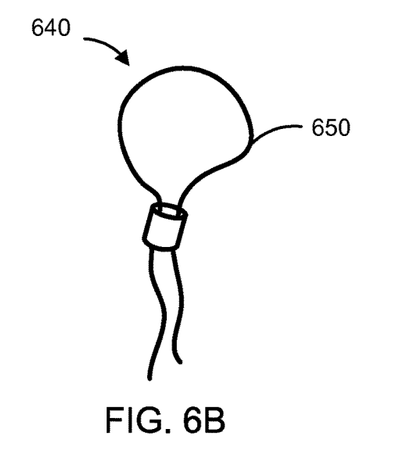
FIG. 6B shows a top view of the retaining cord of FIG. 6A.

FIGS. 6A and 6B illustrate another embodiment of a fluid capturing device 600 that can be removably positioned over at least a part of a penis 605 for collecting fluids. For example, the device 600 can include a sheath 602 and removable absorbent 620 that can be replaced with a new absorbent 620, as described above. For example, the absorbent 620 can be removed from the sheath 602 through a second opening 610 of the sheath 602, including while the sheath 602 is positioned on the penis 605, such as described above. Additionally, the sheath 602 can have a retention feature 640 that can assist with securing the position of the device 600 relative to the penis 605.

The retention feature 640 can include a retaining cord 650 that can extend through a circumferential pocket 651 that is integrated with or coupled to the sheath 602. In addition, the retaining cord 650 can include a securing feature 653 that can releasably secure a position (e.g., via friction) along the retaining cord 650 and can assist with either applying or maintaining a circumferential force applied by the retaining cord 650 around the penis. For example, during use, the securing feature 653 can be loosened (i.e., advanced along the cord towards the distal ends of the cord) in order to allow the penis to be inserted and positioned within the sheath 402. In addition, the securing feature 653 can be tightened (i.e., advanced along the cord away from the distal ends of the cord) in order to allow the retaining cord 650 to apply the circumferential compressive force and assist with securing the sheath 602 to the penis 605.

Figure 7:
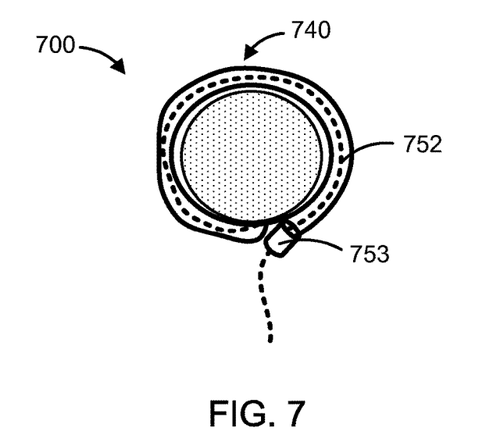
FIG. 7 shows a top view of yet another embodiment of a fluid capturing device positioned over a penis, with the fluid capturing device having a retention feature including a single free-ended retaining cord.

FIG. 7 illustrates another embodiment of a fluid capturing device 700 that can be removably positioned over at least a part of a penis 705 for collecting fluids. For example, the device 700 can include a sheath 702 and removable absorbent 720 that can be replaced with a new absorbent 720, as described above. For example, the absorbent 720 can be removed from the sheath 702 through a second opening 710 of the sheath 702, including while the sheath 702 is positioned on the penis 705, such as described above. Additionally, the sheath 702 can have a retention feature 740 that can assist with securing the position of the device 700 relative to the penis 705.

The retention feature 740 can include a single free-ended retaining cord 752 that can extend through a circumferential pocket 751 that is integrated with or coupled to the sheath 702. In addition, the single free-ended retaining cord 752 can include a securing feature 753 that can releasably secure a position (e.g., via friction) along the single free-ended retaining cord 752 and can assist with either applying or maintaining a circumferential compressive force applied by the single free-ended retaining cord 752 around the penis. A first end of the single free-ended retaining cord 752, for example, can be attached to either the sheath or circumferential pocket 751. A second end of the single free-ended retaining cord 752 can be free to extend from the circumferential pocket 751 and assist with adjusting the circumferential compressive force. The securing feature 753 can also be coupled to the single free-ended retaining cord 752 adjacent the second end for assisting with adjusting and maintaining the circumferential compressive force. For example, during use, the securing feature 753 can be loosened (i.e., advanced along the cord toward the distal free-end) in order to allow the penis to be inserted and positioned within the sheath 702. The securing feature 753 can be tightened (i.e., advanced along the cord away from the distal free-end) in order to allow the single free-ended retaining cord 752 to apply the circumferential compressive force and assist with securing the sheath 702 to the penis 705.

Figure 8A:
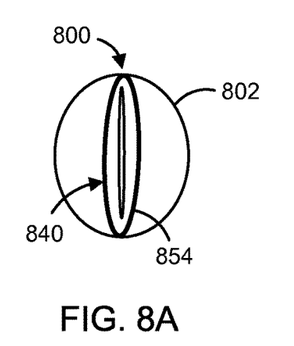
FIG. 8A shows a top view of yet another embodiment of a fluid capturing device having a retention feature including a deformable elastic element in a collapsed state.
Figure 8B:
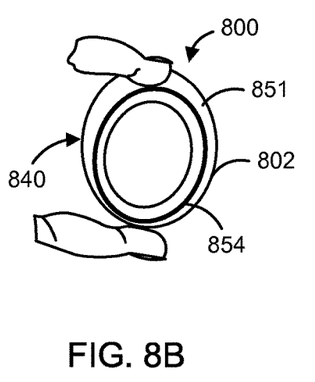
FIG. 8B shows a top view of the deformable elastic element of FIG. 8A in an expanded state.
Figure 8C:
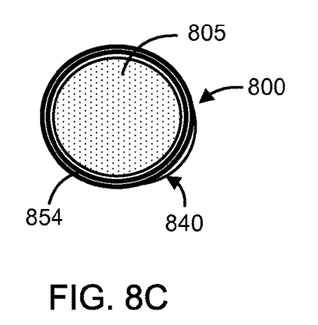
FIG. 8C shows a top view of the deformable elastic element of FIG. 8A in an expanded state and positioned over a penis.

FIG. 8A-8C illustrates another embodiment of a fluid capturing device 800 that can be removably positioned over at least a part of a penis 805 for collecting fluids. For example, the device 800 can include a sheath 802 and removable absorbent 820 that can be replaced with a new absorbent 820, as described above. For example, the absorbent 820 can be removed from the sheath 802 through a second opening 810 of the sheath 802, including while the sheath 802 is positioned on the penis 805, such as described above. Additionally, the sheath 802 can have a retention feature 840 that can assist with securing the position of the device 800 relative to the penis 805.

The retention feature 840 can include a deformable elastic element 854 that can be coupled to the sheath 802, such as extending through a circumferential pocket 851 integrated with or coupled to the sheath 802. The deformable elastic element 854 can apply a circumferential compressive force around the penis and a part of the sheath 802, which can assist with securing the position of the sheath 802 relative to the penis 805. The deformable elastic element 854 can have a ring shape and can be made out of one or more of a variety of materials, including nickel titanium shape memory alloys (nitinol) and flexible, deformable polymers. Additionally, the deformable elastic element 854 can be made in a variety of sizes in order to achieve a desired level of retention of the sheath and comfort for the user.

For example, during use the deformable elastic element 854 can be expanded (as shown in FIG. 8B) from its collapsed position (see FIG. 8A) by compressing the extents of the deformable elastic element 854 in the collapsed position. This can force the deformable elastic element 854 to expand, which can allow the penis 805 to be inserted into the sheath 802 and position the sheath relative to the penis. The deformable elastic element 854 can be released in order to allow the deformable elastic element 854 to partially collapse and apply a circumferential compressive force around the penis, which can allow the deformable elastic element 854 to retain the sheath 802 in a desired position over the penis.

Embodiments of the fluid capturing device discussed herein include a removable and replaceable absorbent, which can include any of the absorbents discussed herein, including any of the absorbent embodiments described below. The absorbents can have a variety of shapes and sizes, including forming more than one shape, such as a compact and expanded shape or configuration. For example, the compact configuration can allow for either improved loading or unloading of the absorbent from the sheath. The absorbent can form the expanded configuration upon either contact with moisture or placement within the sheath, such as within the distal portion. The absorbent can be pre-loaded, such that the fluid capturing device comes with an absorbent already in place in the sheath for use. Alternatively or in addition, the absorbent can either be loaded through the first opening of the sheath or through a slit formed along the sheath (see, for example, FIGS. 22A-22D).

In addition, a grasping feature extending from the absorbent can be used to assist in either positioning the absorbent in the sheath or removing the absorbent from the sheath. The absorbent can be removed, for example, by pulling on the grasping feature in order to pull the absorbent through the second opening in the sheath, including while the user has the sheath secured to the user's penis. As such, the second opening can include a flexible or elastic property that allows the absorbent to be removed through the second opening, while also preventing the absorbent from traveling through the second opening until desired, such as when the user pulls the absorbent out through the second opening. The grasping feature can include an adhesive tape (not shown) or adhesive material at a distal end of the grasping feature, which can allow the user to secure the distal end of the grasping feature (e.g., to the sheath) in order to prevent unintended pulling on the grasping feature. The grasping feature can be made out of the same or different material than the absorbent. For example, the grasping feature can be made out of a hydrophobic material, which can prevent the grasping feature from absorbing fluid and potentially leaking fluid out from the sheath.

Replacement absorbents can be provided, for example, in individual packaging, which can allow for easy and sanitary transport. For example, each absorbent can capture up to approximately 8 mL to approximately 12 mL of fluid, however, an absorbent can capture more or less without departing from the scope of the present disclosure. As will be discussed in greater detail below, the absorbent can be discretely removed and replaced from the sheath, including while the user is wearing the sheath. The slit in the sheath can also allow the user to perform normal functions, such as urinate, without having to remove the sheath completely from the penis (i.e., the retention feature can remain secured).

In addition, although described as an absorbent for collecting fluids, such as bodily fluids (e.g., urine), the absorbent can provide any number of a variety of functions. For example, the absorbent can provide protection, such as for addressing a wound. Alternatively or in addition, the absorbent can be impregnated with at least one medicament for delivery to a part of the penis. Additionally, although the positioning feature is shown and described as a string or tab, the positioning feature can have any shape or size for providing assistance with positioning (e.g., either loading or removing) the absorbent relative to the sheath.

Figure 9A:
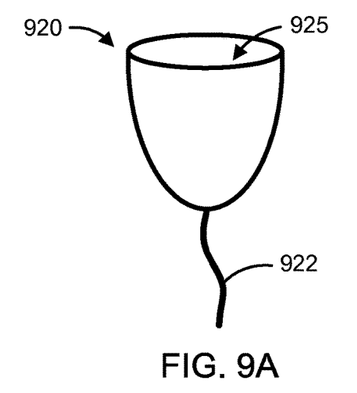
FIG. 9A shows a side view of an embodiment of an absorbent in an expanded configuration.
Figure 9B:
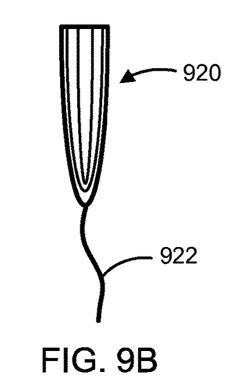
FIG. 9B shows a side view of the absorbent of FIG. 9B in a collapsed configuration.

FIGS. 9A and 9B illustrate an embodiment of an absorbent 920 in an expanded and compact configuration, respectively. The compact configuration, which can have a cylindrical shape, can assist with either inserting or removing the absorbent 920 from the sheath. In addition, the absorbent 920 can be made out of a material that allows the absorbent 920 to expand and contract, such as in response to absorption of fluid, release of a restriction around the absorbent, or any of a variety of ways that can allow the absorbent 920 to form both an expanded and compact configuration. Additionally, the absorbent 920 can have a grasping feature 922 integrated with or secured to the absorbent 920, which can assist with either removal or insertion of the absorbent 920.

At least in the expanded configuration, the absorbent 920 can have a hollow formation that includes a cavity 925. In addition, the absorbent 920 can be sized and shaped to surround at least a part of the distal end of the penis. For example, the absorbent, such as the walls forming the cavity 925, can surround at least the head of the penis. The absorbent can be symmetrical or asymmetrical and can have a variety of shapes and sizes.

Figure 10A:
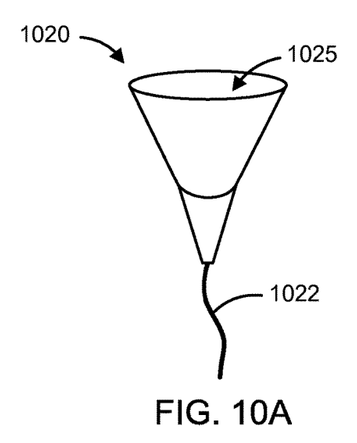
FIG. 10A shows a side view of another embodiment of an absorbent in an expanded configuration.
Figure 10B:
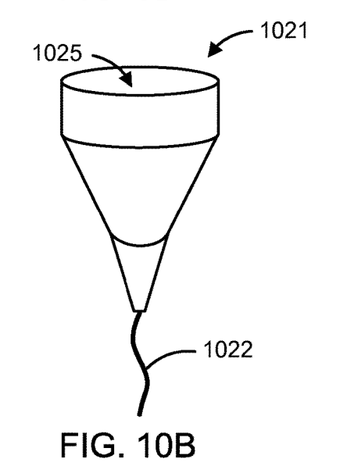
FIG. 10B shows a side view of yet another embodiment of an absorbent in an expanded configuration.

FIG. 10A illustrates another embodiment of an absorbent 1020 in an expanded configuration with a grasping feature 1022 either integrated with or coupled to the absorbent 1020. The absorbent 1020 can have a hollow formation that includes a cavity 1025. In addition, the absorbent can include one or more continuous planar surfaces, which can form conical and cylindrical formations. FIG. 10B illustrates another embodiment of an absorbent 1021 in an expanded configuration, which also includes one or more planar surfaces. The absorbents 1020 and 1021 can form both an expanded and compact configuration.

Figure 11A:
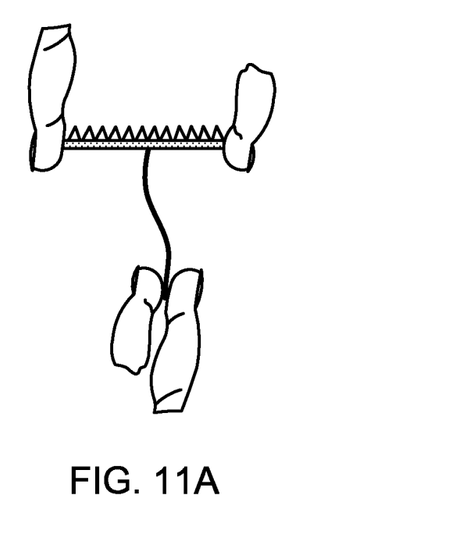
FIG. 11A shows a side view of yet another embodiment of an absorbent in a collapsed configuration.
Figure 11B:
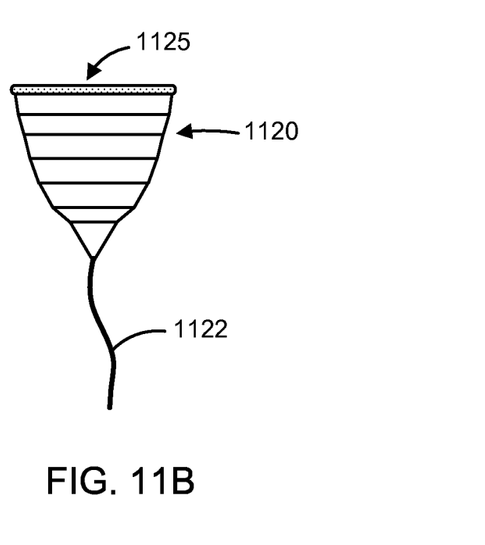
FIG. 11B shows a side view of the absorbent of FIG. 11A in an expanded configuration.

FIGS. 11A and 11B illustrate another embodiment of an absorbent 1120 in a collapsed and expanded configuration, respectively. The absorbent can be made out of a convoluted pattern that can allow the absorbent 1120 to collapse into a flat formation, as shown in FIG. 11A. For example, a user can pull on a grasping feature 1122 coupled to an outer surface of the absorbent 1120, which can cause the absorbent 1120 to expand into the expanded configuration, as shown in FIG. 11B. The collapsed configuration can allow for easy and discrete transportation of the absorbent 1120 and the expanded configuration can have a hollow formation that includes a cavity 1125.

Figure 12A:
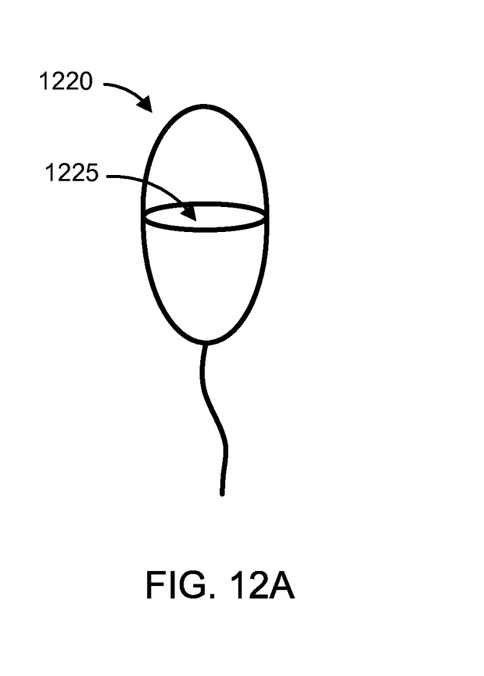
FIG. 12A shows a first side view of yet another embodiment of an absorbent having an asymmetric structure.
Figure 12B:
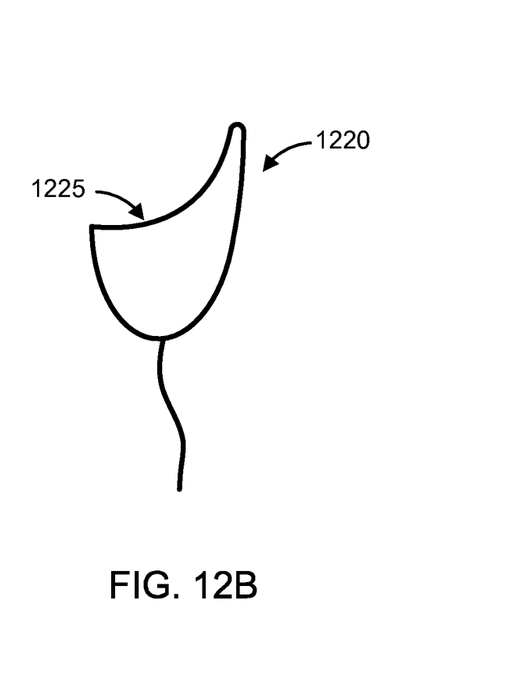
FIG. 12B shows a second side view of the absorbent of FIG. 12A.

FIGS. 12A and 12B illustrate another embodiment of an absorbent 1220 having an asymmetric structure. The absorbent 1220 can also have a hollow formation that includes a cavity 1225 and can form a compact and expanded configuration. For example, the elongated side of the absorbent 1220 can account for anatomical features and positioning of the penis within the sheath.

Figure 13:
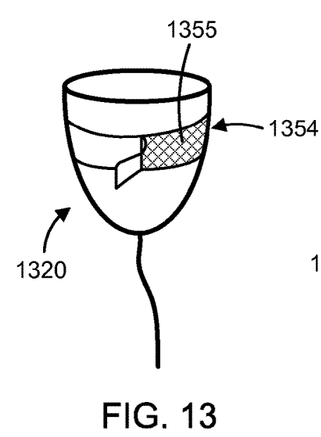
FIG. 13 shows a side view of yet another embodiment of an absorbent having an external positioning feature including an adhesive.
Figure 14:
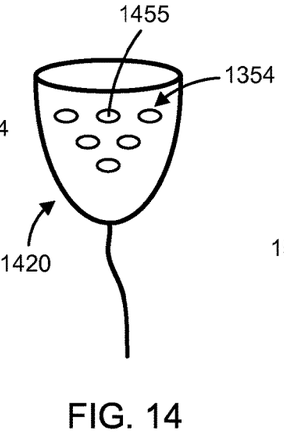
FIG. 14 shows a side view of yet another embodiment of an absorbent having external positioning feature including at least one rounded protrusion.
Figure 15:
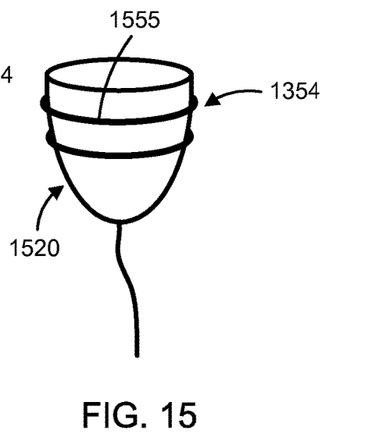
FIG. 15 shows a side view of yet another embodiment of an absorbent having external positioning feature including at least one ring.

FIGS. 13-15 illustrate additional embodiments of an absorbent including an external positioning feature 1354, which can assist with securing the position of the absorbent within the sheath, such as within the distal portion of the sheath. One or more of a variety of external features 1354 can be included along a surface of the absorbent, including any of the absorbent embodiments discussed herein. For example, the external features 1354 can include an adhesive, a hook and loop type fastener system, a mechanical interlocking surface that can grip or otherwise adhere to an inner surface of the sheath, and/or one or more extruded geometric features.

FIG. 13 illustrates an absorbent 1320 with an embodiment of an external feature 1354 including an adhesive or tape 1355, which can include a peel-away liner. In addition, FIG. 14 illustrates an absorbent 1420 with an embodiment of an external feature 1354 including extruded geometric features, such as raised spherical features 1455, that can assist with securing (e.g., via friction) the absorbent within the sheath. Additionally, FIG. 15 illustrates an absorbent with an embodiment of an external feature 1354 including extruded geometric features, such as one or more raised rings 1555, that can assist with securing (e.g., via friction) the absorbent within the sheath.

Figure 16:
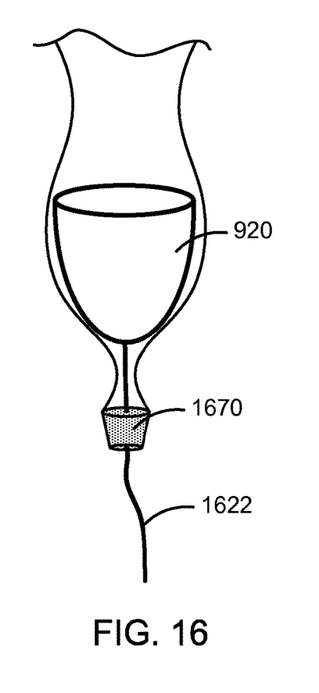
FIG. 16 shows a side view of an absorbent coupled to a grasping feature including an embodiment of a securing feature having a tapered cylinder configuration, the securing feature being configured to assists with positioning the absorbent relative to the sheath.
Figure 17:
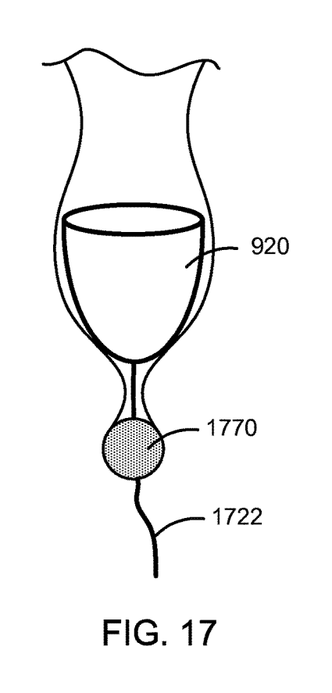
FIG. 17 shows a side view of an absorbent coupled to a grasping feature having another embodiment of a securing feature having a spherical configuration.

FIG. 16 illustrates an absorbent, such as the absorbent 920 shown in FIGS. 9A and 9B, coupled to a grasping feature 1622 that includes an embodiment of a securing feature 1670 having a tapered cylinder configuration. For example, the securing feature 1670 can assist with positioning the absorbent relative to the sheath, such as by preventing the absorbent from migrating from the distal end of the sheath to the proximal end of the sheath. The securing feature 1670 can be any of a variety of shapes and sizes. For example, as shown in FIG. 17, the absorbent 920 can be coupled to a grasping feature 1722 that includes an embodiment of a securing feature 1770 having a rounded or spherical configuration.

Figure 18:
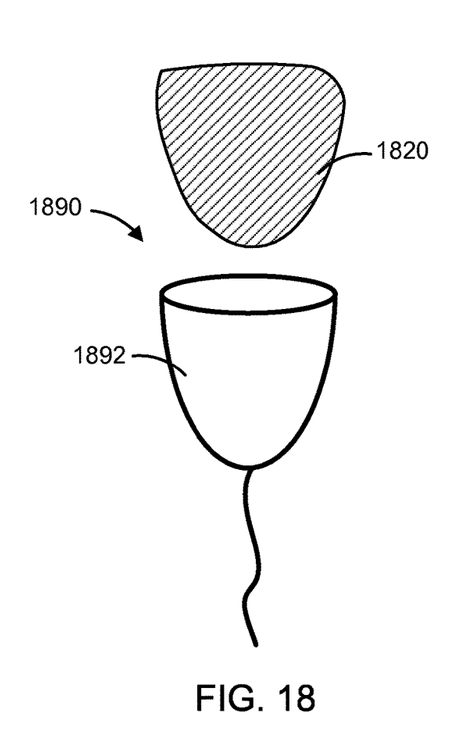
FIG. 18 shows an exploded view of an absorbent structure including a reusable component and an absorbent that can be at least partially contained within the reusable component.

FIG. 18 illustrates an absorbent structure 1890 that includes a reusable component 1892 and an absorbent 1820, which can be disposable. During use, the absorbent 1820 can be secured to and at least partially contained within the reusable component 1892. In addition, the reusable component 1892 can be secured to a sheath, such as within a distal portion of the sheath. For example, the reusable component 1892 can be washed and/or sanitized such that it can be reused. In addition, the absorbent 1820 can be removed from the reusable component 1892 and replaced with a new absorbent. Additionally, some embodiments of the absorbent (including any of the absorbent embodiments disclosed herein) can be reusable, such as an absorbent that can be cleaned and/or sanitized for re-use.

Figure 19:
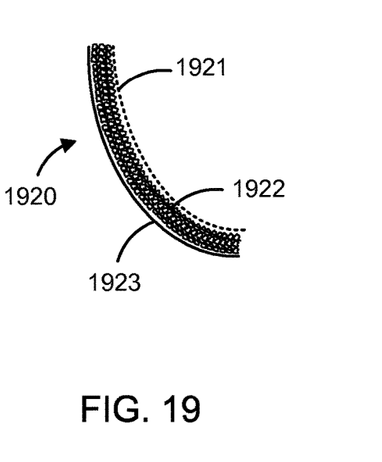
FIG. 19 shows a cross-section view of a part of an absorbent including more than one type of material, such as a directionally permeable material, an absorbent material, and a moisture resistant material.

As shown in FIG. 19, an absorbent 1920 can include one or more layers of materials, including a directionally permeable material 1921, an absorbent material 1922, and a moisture resistant material 1923. In addition, the layer of material forming the inner surface of the absorbent (i.e., positioned closest to the penis during use), can include the directionally permeable material 1921, which can assist in directing fluid or moisture away from the penis. The absorbent 1920 can include the absorbent material 1922 layer adjacent the directionally permeable material layer 1921 in order to allow the absorbent material 1922 to absorb and contain the fluid or moisture collected from the penis. Additionally, the absorbent 1920 can include a moisture barrier 1923 that forms an outer surface of the absorbent, which can assist in containing the fluid and moisture within the absorbent.

The absorbent can be made out of one or more of a variety of materials. For example, the absorbent can include hydro gels, hydroxyl ethyl cellulose, silica gels, polymethlymethacrylate gels, clays, etc. The absorbent material can be woven, non-woven, extruded, calendered, knitted, spin bonded, etc. In addition, the outer surface of the absorbent can include a material that is impervious to the passage of aqueous based fluids, which can be the result of physical properties of the material and/or can be supplied by supplemental processing, treatments, additives, etc. In addition, the outer surface can allow the passage of air through it in either a preferential direction or bi-directionally. The various components and materials of the absorbent can be assembled and secured together using techniques such as, but not limited to, adhesive bonding, thermal bonding, crimping or other mechanical deformation, sewing, etc.

Figure 20:
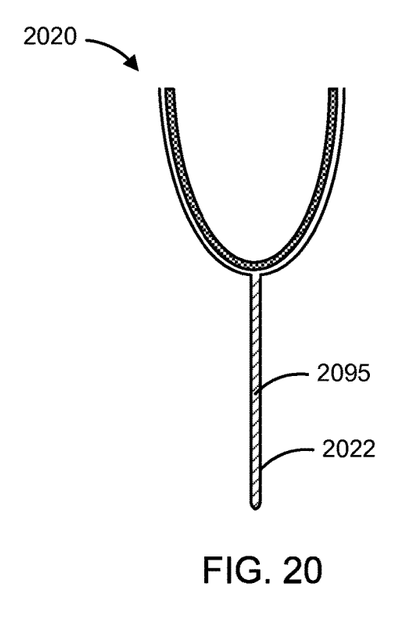
FIG. 20 shows a cross-section view yet of another embodiment of an absorbent having a grasping feature including an integrated tab.

FIG. 20 illustrates another embodiment of an absorbent 2020 having a grasping feature 2022 including an integrated tab 2095. For example, the integrated tab 2095 can be formed by bonding or adhering one or more materials of the absorbent together. The integrated tab 2095 can have any number of a variety of shapes and sizes.

Figure 21:
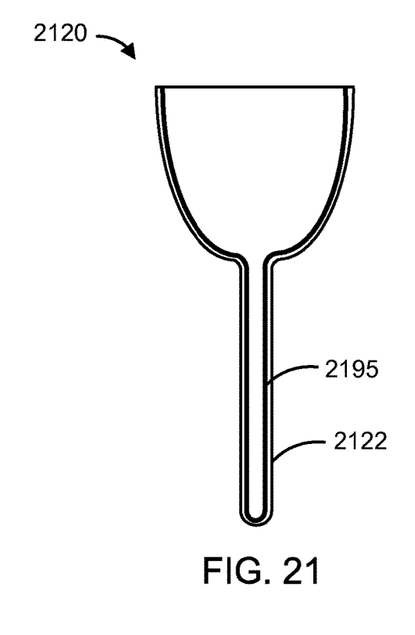
FIG. 21 shows a cross-section view of yet another embodiment of an absorbent having a grasping feature including an integrated seam.

FIG. 21 illustrates another embodiment of an absorbent 2120 having a grasping feature 2122 including an integrated seam 2195. For example, the integrated seam 2195 can be formed by a cord or string that is incorporated into the absorbent, as shown in FIG. 21.

The various fluid capturing devices disclosed herein can be used to cover at least a part of a penis and collect one or more of a variety of fluids. While exemplary methods are discussed below for positioning the fluid capturing device on a penis, as well as removing and replacing an absorbent, a person skilled in the art will appreciate that the fluid removal devices are not limited to the exemplary methods discussed herein.

FIGS. 22A-22D schematically illustrate one exemplary method of using a fluid capturing device having a removable absorbent, which can be replaced with a new absorbent. The method detailed below can be used with any of the devices and features disclosed above (e.g., the fluid capturing device 100, 200, 300, 400, 500, 600, 700, the absorbent 920, 1020, 1021, 1120, 1220, 1320, 1420, 1520, 2020, 2120, etc.), with any necessary modifications being apparent to one skilled in the art having read the above disclosure. By way of example, the method is described in connection with fluid capturing device 100 of FIG. 1.

To begin with, a distal end of a penis 105 of a user can be inserted into the sheath 102, such as through the first opening 108 of the proximal portion 104. The penis 105 can be inserted until either the proximal portion 104 is positioned adjacent a proximal end of the penis 105 or the head of the penis 105 is positioned within at least a part of the distal portion 106 of the sheath 102. In addition, the sheath 102 can be secured in position relative to the penis by the retention feature, including at least any of the retention features disclosed herein.

The user can wear the fluid capturing device 100 for a period of time (e.g., one or more hours, days, etc.). For example, the sheath 102 can be made out of material that allows for continuous use and wearing of the fluid capturing device 100. In addition, any part of the fluid capturing device 100, including either the sheath 102 or absorbent 120, can be removed and washed for subsequent wearing and use by the user. Furthermore, as discussed above, the fluid capturing device 100 can be worn while the absorbent 120 is removed from the sheath and also while a new absorbent 120 is inserted into the sheath 102, as will be described in greater detail below.

Figure 22A:
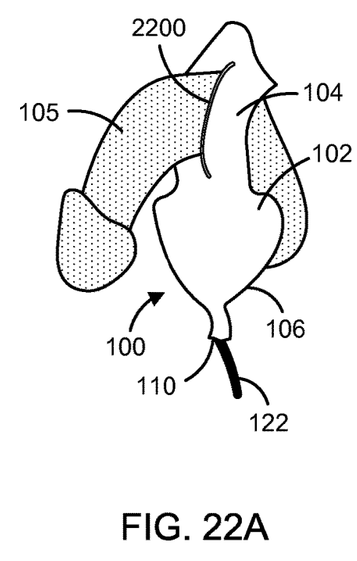
FIGS. 22A-22D schematically illustrate a method of using the fluid capturing device of FIG. 1, including removing and replacing the absorbent.

FIG. 22A illustrates the fluid capturing device 100 secured to the penis 105 while a part of the penis is removed from the sheath 102 through a slit 2200. The slit 2200 can provide a way for the user to discretely and easily remove the penis from the sheath, such as for urinating, without having to release the retention feature 140 and remove the sheath 102 completely from the penis.

Figure 22B:
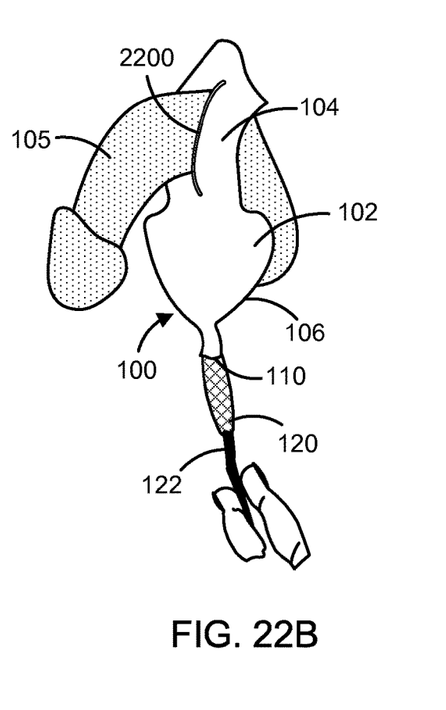

FIG. 22B illustrates a user pulling on the grasping feature 122 and pulling the absorbent 120 out from the sheath 102 through the second opening 110. In addition, the absorbent 120 can be removed while the sheath 102 is secured to the penis 105. Additionally, although the penis is shown as being withdrawn through the slit 2200 while the absorbent 120 is being removed, the penis can alternatively be contained within the sheath 102 (i.e., not withdrawn through the slit 2200) while the absorbent 120 is being removed.

Figure 22C:
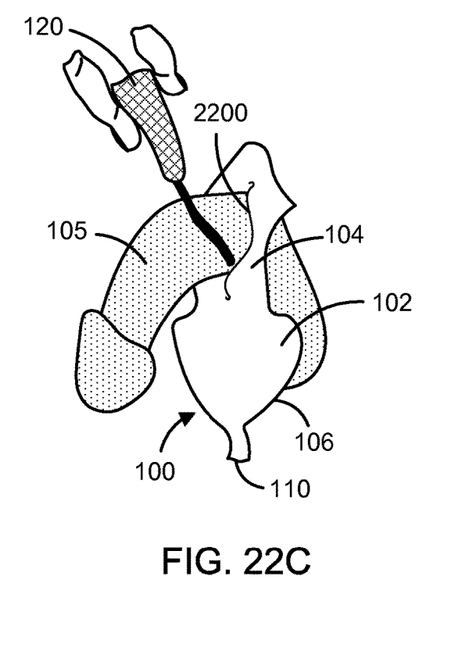
Figure 22D:
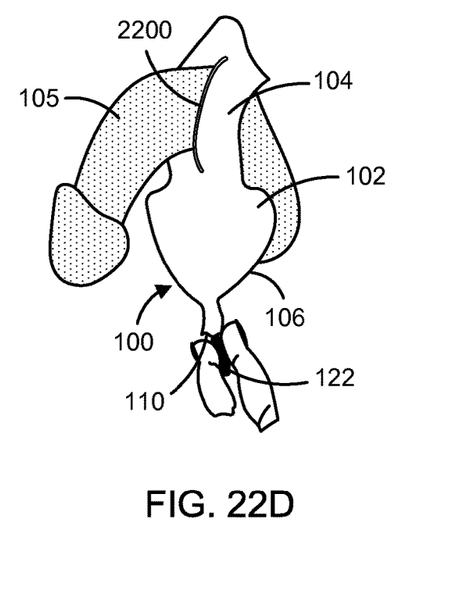

As shown in FIG. 22C, a new absorbent 120 can be inserted into the sheath 102 through the slit 2200. For example, a user can insert the new absorbent 120 through the slit 2200, including with the new absorbent 120 in a compact configuration. In addition, the user can use the grasping feature 122, which can extend through the second opening 110, to position the absorbent within the distal portion 106 of the sheath, as shown in FIG. 22D.

Additionally or in the alternative, a new absorbent 120 can be inserted into the sheath 102 through the first opening 108, or any other openings provided in the sheath 102. For example, the absorbent 120 can be inserted in a compact configuration and can expand into an expanded configuration once positioned within the sheath 102. In addition, although the penis is shown as being withdrawn through the slit 2200 while the new absorbent 120 is being inserted, the penis can alternatively be contained within the sheath 102 (i.e., not withdrawn through the slit 2200) while the new absorbent 120 is being inserted.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A fluid capturing device for positioning over at least a part of a penis, comprising:
    a sheath including a proximal portion that is tubular for extending around at least a part of a shaft of a penis and a distal portion that is contoured to cover at least a part of a head of the penis, the proximal portion including a first opening having a first diameter and the distal portion including a second opening having a second diameter;
    the second diameter is smaller than the first diameter;
    an absorbent positioned along an inner surface of the sheath, the absorbent configured to be removable through the second opening; and
wherein the absorbent includes a reusable component and a disposable component.

2. The fluid capturing device of claim 1, wherein the sheath includes a retention feature that assists in securing the position of the sheath relative to the penis.

3. The fluid capturing device of claim 2, wherein the retention feature includes a rolled cuff positioned at a proximal end of the sheath.

4. The fluid capturing device of claim 2, wherein the retention feature includes an external flap that is configured to form a secured position and an unsecured position.

5. The fluid capturing device of claim 2, wherein the retention feature includes a compressive sleeve positioned at a proximal end of the sheath.

6. The fluid capturing device of claim wherein the retention feature includes a retaining ring that is configured to provide a circumferential compressive force around a part of the sheath.

7. The fluid capturing device of claim 2, wherein the retention feature includes an adjustable retaining cord that extends through a circumferential pocket at a proximal end of the sheath.

8. The fluid capturing device of claim 2, wherein the retention feature includes a deformable elastic element extending through a circumferential pocket at a proximal end of the sheath.

9. The fluid capturing device of claim 1, further comprising a grasping feature that is at least one of coupled to or integrated with the absorbent, wherein the grasping feature is configured to assist with at least removing the absorbent from the sheath.

10. The fluid capturing device of claim 1, wherein the absorbent is made out of at least one of a directionally permeable material, an absorbent material, and a moisture resistant material.

11. The fluid capturing device of claim 1, wherein the absorbent includes at least one external positioning feature for assisting with securing the positioning of the absorbent relative to the sheath.

12. The fluid capturing device of claim 11, wherein the external positioning feature includes one or more of an adhesive and an extruded geometric feature.

13. The fluid capturing device of claim 1, wherein the absorbent forms a collapsed configuration and an expanded configuration.

14. The fluid capturing device of claim 1, wherein the absorbent includes a hollow shape having a cavity that is adapted to cover at least a part of the head of the penis.

15. A method, comprising:
inserting a part of a penis into a fluid capturing device, the fluid capturing device having a sheath including a proximal portion that is tubular for extending around at least a part of a shaft of the penis and a distal portion that is contoured to cover at least a part of a head of the penis, the proximal portion including a first opening having a first diameter and the distal portion including a second opening having a second diameter, wherein the second diameter is smaller than the first diameter, the fluid capturing device further including an absorbent positioned along an inner surface of the sheath, the absorbent configured to be removable through the second opening and wherein the absorbent includes a reuseable component and a disposable component.

16. The method of claim 15, further comprising removing the absorbent from the fluid capturing device while the sheath is secured to the penis.

17. The method of claim 16, wherein the absorbent is removed from the sheath through the second opening.

18. The method of claim 16, further comprising inserting a new absorbent into the sheath through a slit along a side of the sheath, wherein the new absorbent is inserted while the sheath is secured to the penis.

19. The method of claim 15, further comprising securing the sheath to the penis with a retention feature.

* * * * *